(12) United States Patent
Rotstein et al.

(10) Patent No.: US 9,114,248 B2
(45) Date of Patent: Aug. 25, 2015

(54) ELECTRODE FOR FINDING POINTS OF LOW IMPEDANCE AND APPLYING ELECTRICAL STIMULATION THERETO

(75) Inventors: Hector Rotstein, Haifa (IL); Michael Naroditsky, Carmiel (IL); David Arlinsky, Atlit (IL); Ori Kanner, Burgeta (IL)

(73) Assignee: Nervomatrix Ltd., Netanya (IL)

( * ) Notice: Subject to any disclaimer, the term of this patent is extended or adjusted under 35 U.S.C. 154(b) by 0 days.

(21) Appl. No.: 13/877,457

(22) PCT Filed: Oct. 4, 2011

(86) PCT No.: PCT/IL2011/000776
§ 371 (c)(1),
(2), (4) Date: Apr. 3, 2013

(87) PCT Pub. No.: WO2012/046231
PCT Pub. Date: Apr. 12, 2012

(65) Prior Publication Data
US 2013/0190852 A1    Jul. 25, 2013

Related U.S. Application Data

(60) Provisional application No. 61/389,307, filed on Oct. 4, 2010.

(51) Int. Cl.
*A61N 1/05*    (2006.01)
*A61N 1/36*    (2006.01)

(52) U.S. Cl.
CPC .......... *A61N 1/0502* (2013.01); *A61N 1/36017* (2013.01)

(58) Field of Classification Search
CPC ... A61N 1/0502; A61N 1/36017; A61N 1/05; A61N 1/36014; A61N 1/36
USPC ............................... 607/2, 116; 600/306, 382
See application file for complete search history.

(56) References Cited

U.S. PATENT DOCUMENTS 2,763,935 A * 9/1956 Whaley et al. .................. 33/511
3,154,067 A * 10/1964 Stenstrom et al. ............ 600/500
(Continued)

OTHER PUBLICATIONS

International Search Report issued by USPTO with mailing date of May 4, 2012, for parallel PCT application PCT/IL2011/00776, published as WO 2012/046231 A2 on Apr. 12, 2012.
(Continued)

*Primary Examiner* — Christopher A Flory
(74) *Attorney, Agent, or Firm* — Simo Kahn; Chanoch Kahn

(57) ABSTRACT

An electrode constituted of: a fixture arranged for connection to a frame; and a probe exhibiting a closed face and a generally conically shaped protrusion extending longitudinally from the closed face towards an apex, the probe in communication with the fixture, wherein the fixture is arranged to allow the probe to travel in a generally unrestricted manner exclusively along a longitudinal axis of the probe, wherein the generally conically shaped protrusion is arranged such that when the closed face is in contact with a skin surface, the generally conically shaped protrusion penetrates an outer layer of the skin surface responsive to the weight of the probe and is in electrical contact with an inner portion of the penetrated skin surface, and wherein a portion of the closed face, surrounding the generally conically shaped protrusion, is arranged to be in electrical contact with the outer skin layer.

13 Claims, 4 Drawing Sheets

(56) References Cited

U.S. PATENT DOCUMENTS

| | | | |
|---|---|---|---|
| 4,838,272 A | 6/1989 | Lieber | |
| 5,070,873 A | 12/1991 | Graupe et al. | |
| 5,361,762 A * | 11/1994 | Gunter | 600/372 |
| 5,433,739 A * | 7/1995 | Sluijter et al. | 607/99 |
| 5,449,378 A * | 9/1995 | Schouenborg | 607/46 |
| 5,560,372 A | 10/1996 | Cory | |
| 5,643,306 A * | 7/1997 | Schraga | 606/182 |
| 5,969,821 A * | 10/1999 | Muramatsu et al. | 356/613 |
| 6,141,575 A | 10/2000 | Price | |
| 6,510,975 B2 * | 1/2003 | Enomoto | 228/112.1 |
| 6,564,079 B1 | 5/2003 | Cory et al. | |
| 6,850,795 B2 | 2/2005 | Hoium et al. | |
| 8,014,873 B2 * | 9/2011 | Jones et al. | 607/117 |
| 8,271,065 B1 * | 9/2012 | Wilson et al. | 600/383 |
| 8,355,790 B2 * | 1/2013 | Naroditsky et al. | 607/46 |
| 2001/0029373 A1 * | 10/2001 | Baker et al. | 606/49 |
| 2002/0133149 A1 * | 9/2002 | Bessette | 606/41 |
| 2002/0188332 A1 | 12/2002 | Lurie et al. | |
| 2003/0078643 A1 * | 4/2003 | Schulman et al. | 607/116 |
| 2003/0135245 A1 | 7/2003 | Campos | |
| 2003/0139678 A1 | 7/2003 | Hoium et al. | |
| 2003/0195599 A1 | 10/2003 | Bishay | |
| 2004/0082842 A1 * | 4/2004 | Lumba et al. | 600/338 |
| 2004/0147977 A1 | 7/2004 | Petrovsky | |
| 2005/0070841 A1 * | 3/2005 | Mathiesen et al. | 604/20 |
| 2005/0159797 A1 * | 7/2005 | Chandran et al. | 607/99 |
| 2005/0288759 A1 * | 12/2005 | Jones et al. | 607/116 |
| 2006/0041241 A1 * | 2/2006 | Herndon | 604/500 |
| 2006/0047194 A1 | 3/2006 | Grigorov | |
| 2006/0085056 A1 | 4/2006 | Schouenborg | |
| 2007/0167943 A1 * | 7/2007 | Janssen et al. | 606/41 |
| 2008/0009763 A1 * | 1/2008 | Chiou et al. | 600/544 |
| 2008/0081976 A1 * | 4/2008 | Hodges et al. | 600/345 |
| 2009/0171339 A1 * | 7/2009 | Young et al. | 606/33 |
| 2009/0198305 A1 | 8/2009 | Naroditsky et al. | |
| 2010/0114095 A1 * | 5/2010 | Janssen et al. | 606/41 |
| 2011/0009929 A1 * | 1/2011 | Nuccitelli et al. | 607/72 |
| 2011/0040237 A1 * | 2/2011 | Herndon | 604/20 |
| 2011/0046626 A1 * | 2/2011 | Herndon | 606/80 |
| 2011/0190659 A1 * | 8/2011 | Long et al. | 600/564 |
| 2012/0330125 A1 * | 12/2012 | Wilson et al. | 600/383 |

OTHER PUBLICATIONS

Written Opinion of the International Searching Authority with mailing date of May 4, 2012, for parallel PCT application PCT/IL2011/00776, published as WO 2012/046231 A2 on Apr. 12, 2012.

M.I. Johnson, "Acupuncture-like Transcutaneous Electrical Nerve Stimulation (AL-TENS) in the Management of Pain", Physical Therapy Reviews, vol. 3, published 1998, pp. 73-93.

* cited by examiner

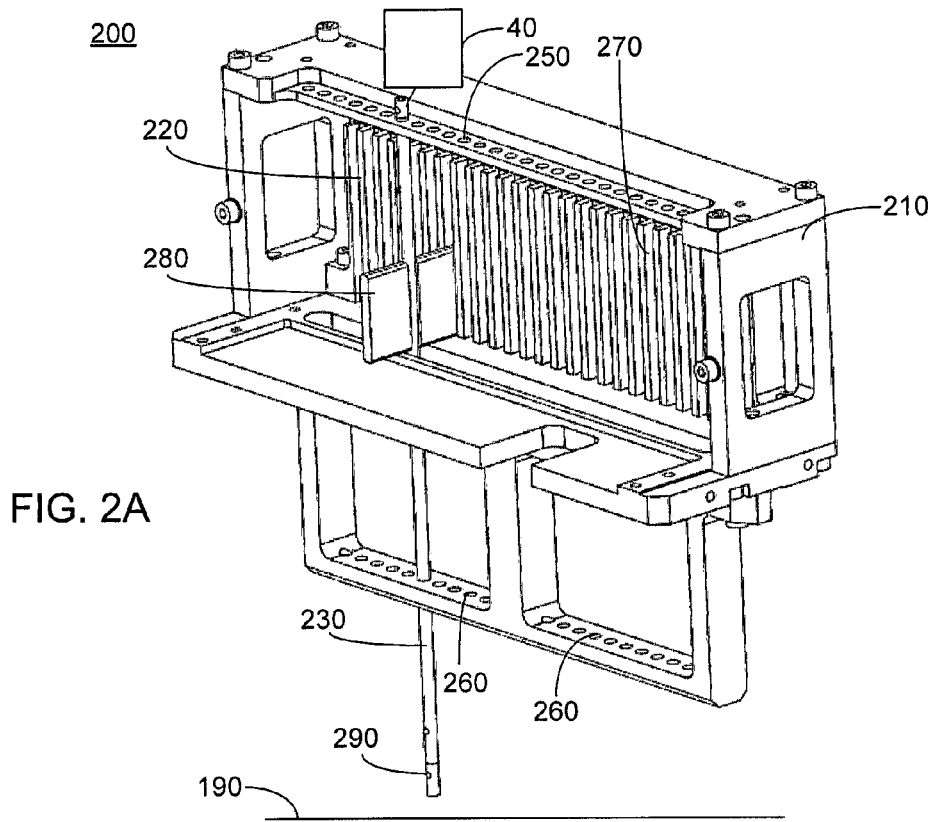
FIG. 2A
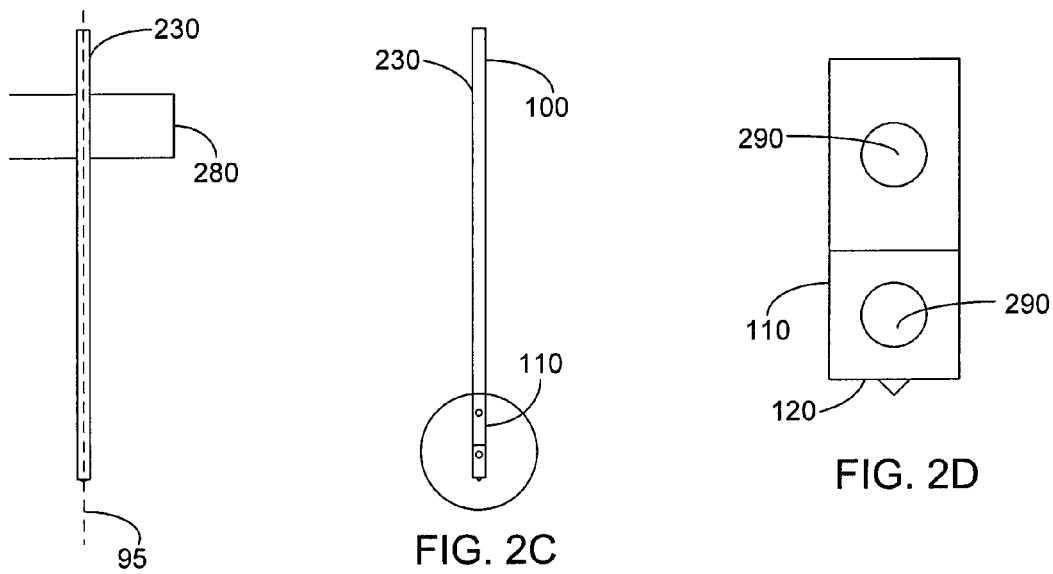
FIG. 2B
FIG. 2C
FIG. 2D

ELECTRODE FOR FINDING POINTS OF LOW IMPEDANCE AND APPLYING ELECTRICAL STIMULATION THERETO

TECHNICAL FIELD

The present invention relates generally to the field of electrodes for finding points on the human body exhibiting low electrical impedance and applying electrical stimulation thereto.

BACKGROUND

Medical practice shows that points in the skin of the human body exhibiting low electrical impedance are consonant with the location of pain sensation, and that providing electrical stimulation to those points can reduce the pain sensation temporarily. Moreover, if electrical stimulation is applied in a plurality of sessions over several days, the pain sensation can be reduced for long periods of time. Several devices and methods have been introduced for localizing the points exhibiting low impedance, and applying electrical stimulation thereto. One device is the Pointer Excel II Device, manufactured by TENS PLUS Industrial Company of Kwun Tong, Hong Kong, which consists of an apparatus comprising a probe for exploring the desired area of the body of the patient and searching for points exhibiting reduced impedance. When one such point is identified, the same apparatus is used to stimulate the point exhibiting low impedance using electrical currents. The electrode used for finding the points and providing the electrical stimulation consists of a metal rod with one end mechanically and electrically attached to the body of the apparatus and the other end having a round, ball-like termination that is pressed to the skin. It is well known that for this class of electrodes the amount of force applied to the skin during the low impedance detection phase affects the impedance measurement and consequently, for good results, the device must be operated by an individual skilled in finding points exhibiting low impedance. When used by an individual who is not sufficiently skilled, the device may not identify points exhibiting low impedance. Alternatively, a point that does not exhibit low impedance may be identified as exhibiting low impedance and electrical stimulation may be inappropriately applied without causing the desired effect.

An alternative device has been introduced, containing a plurality of sharp metal points or needles that are mounted on a flexible pad and applied to the skin with the sharp edges applying force on the skin and the other end mechanically supported by the flexible pad. An end of the pad is electrically connected to an electronic circuit that probes each needle, one at a time, determines if the point of the skin juxtaposed with the needle exhibits low impedance and, in the event that the point exhibits low impedance, applies electrical stimulation to that point. Unfortunately, because the needles are probed individually, the force applied to the skin by the plurality of needles may not be uniform and consequently the resulting impedance measurement is not reliable. Moreover, the sharp points have a reduced area for electrical connectivity with the skin, thereby complicating the supply of the relatively large voltage required for the electrical stimulation.

U.S. patent application Ser. No. 12/301,464, filed Nov. 19, 2008 to Naroditsky, the entire contents of which are incorporated herein by reference, describes a device wherein a plurality of electrodes in the form of metal rods are mechanically positioned in at least one array. The rods can move freely in a longitudinal direction such that when the device is juxtaposed with the skin the electrodes advance onto the skin thereby applying force depending solely on the weight of the electrode. If all the electrodes have the same weight, the force will be uniform. In this configuration, one end of the electrode applies force to the skin while the other end of the electrode is electrically connected to an electronics circuit that can probe each electrode and determine if the area of the skin juxtaposed with the particular electrode exhibits a low impedance, and in the event that the area of the skin exhibits low impedance, apply electrical stimulation to the area of skin via the electrode. Unfortunately, the electrodes measure the impedance of the outer layer of the skin which exhibits relatively high impedance. Thus, the high impedance of the outer layer of the skin may interfere with the measurement of the low impedance of the inner layers of the skin.

A technical paper titled "Mapping Acupuncture Points Using Multi-channel Device" by G. Kwok, M. Cohen and I. Cosic, describes a device wherein each electrode is a small diameter metallic pin which can penetrate the outer layer of the skin and thus measure the impedance of the inner layers of the skin. Disadvantageously, the penetration is performed in an uncontrolled manner which can cause inconsistencies in the impedance measurement. Additionally, due to their small size, a disposable device cannot be attached to the pins.

SUMMARY

Accordingly, it is a principal object to overcome at least some of the disadvantages of the prior art. This is accomplished in certain embodiments by providing an electrode comprising: a fixture arranged for connection at one end thereof to a frame; and a probe, the probe exhibiting a closed face and a generally conically shaped protrusion extending longitudinally from the closed face towards an apex, the probe in communication with the fixture, the closed face opposing the end arranged for connection to the frame, wherein the fixture is arranged to allow the probe to travel in a generally unrestricted manner exclusively along a longitudinal axis of the probe. The generally conically shaped protrusion is arranged such that when the closed face is in contact with a skin surface, the generally conically shaped protrusion penetrates an outer layer of the skin surface responsive to the weight of the probe, and a portion of the closed face, surrounding the generally conically shaped protrusion, is thus arranged to be in electrical contact with the outer layer of the skin surface.

In one embodiment, the generally conically shaped protrusion extends longitudinally for 0.2-5 mm from the closed face of the probe. In another embodiment, the maximal dimension of the face of the probe is 1.5-10 mm, and the generally conically shaped protrusion extends longitudinally from the face of the probe for 0.2 mm-50% of the maximal dimension of the closed face.

In one embodiment, the base of the generally conically shaped protrusion exhibits a maximal dimension of 0.2 mm-50% of the maximal dimension of the closed face. In another embodiment, the probe exhibits a weight of 20-120 grams. In another embodiment, the probe is constituted of an electrically conducting material, and is further in electrical communication with an electrical measurement and electrical stimulation circuitry.

In one further embodiment, the probe is one of: an elongate cylinder shape; an elongate elliptical shape and a rectangular shape. In another further embodiment, the fixture exhibits a base portion for connection to a frame and is generally cylindrical in shape, and the probe is an open cylinder generally surrounding the fixture.

In one further embodiment, the fixture is further arranged to restrain the probe so as to allow the probe to travel along the longitudinal axis of the probe responsive solely to gravity. In another further embodiment, the probe is arranged to travel along the longitudinal axis of the probe responsive to the advancement of one of: a spring; a hydraulic device and an air pressure device.

In one further embodiment, the closed face further exhibits a perimeter protrusion extending longitudinally from the perimeter area of the closed face of the probe, the perimeter protrusion proceeding in parallel with the generally conically shaped protrusion, the perimeter protrusion proceeding from a base towards an edge, wherein the perimeter protrusion is arranged such that when the closed face is in contact with a skin surface, the perimeter protrusion penetrates an outer layer of the skin surface responsive to the weight of the probe.

In one yet further embodiment, the generally conically shaped protrusion, the perimeter protrusion and the closed face of the probe generally form an open horn torus. In another yet further embodiment, the extension of the perimeter protrusion is 80%-120% of the extension of the generally conically shaped protrusion. In another yet further embodiment, the base of the perimeter protrusion exhibits a thickness of 0.1 mm-90% of the maximal dimension of the closed face.

In one independent embodiment an apparatus is provided, comprising: a frame; an array of fixtures, each connected to the frame at a predetermined location; and a plurality of probes, each of the probes exhibiting a closed face and a generally conically shaped protrusion extending longitudinally from the closed face towards an apex, each of the probes in communication with a particular one of the fixtures, the closed face of the probe opposing the connection of the particular fixture to the frame, wherein each of the fixtures is arranged to allow the probe to travel in a generally unrestricted manner exclusively along a longitudinal axis of the probe, wherein the generally conically shaped protrusion is arranged such that when the closed face is in contact with a skin surface, the generally conically shaped protrusion penetrates an outer layer of the skin surface responsive to the weight of the probe, and wherein a portion of the closed face, surrounding the generally conically shaped protrusion, is arranged to be in electrical contact with the outer layer of the skin surface.

In one embodiment, the apparatus further comprises an electrical measurement and electrical stimulation circuitry, the electrical measurement and electrical stimulation circuitry in electrical communication with each of the probes.

In another independent embodiment, an electrode is provided comprising: a probe, the probe exhibiting a closed face and a generally conically shaped protrusion extending longitudinally from the closed face towards an apex; and a means for allowing the probe to travel in a generally unrestricted manner exclusively along a longitudinal axis of the probe, wherein the generally conically shaped protrusion is arranged such that when the closed face is in contact with a skin surface, the generally conically shaped protrusion penetrates an outer layer of the skin surface responsive to the weight of the probe, and wherein a portion of the closed face, surrounding the generally conically shaped protrusion, is arranged to be in electrical contact with the outer layer of the skin surface.

In one embodiment, the generally conically shaped protrusion extends longitudinally for 0.2-5 mm from the closed face of the probe. In another embodiment, the maximal dimension of the face of the probe is 1.5-10 mm, and the generally conically shaped protrusion extends longitudinally from the face of the probe for 0.2 mm-50% of the maximal dimension of the closed face. In one further embodiment, the base of the generally conically shaped protrusion exhibits a maximal dimension of 0.2 mm-50% of the maximal dimension of the closed face.

In one embodiment, the probe exhibits a weight of 20-120 grams. In one further embodiment, the face further exhibits a perimeter protrusion extending longitudinally from the perimeter area of the closed face of the probe, the perimeter protrusion proceeding in parallel with the generally conically shaped protrusion, the perimeter protrusion proceeding from a base towards an edge, wherein the perimeter protrusion is arranged such that when the closed face is in contact with a skin surface, the perimeter protrusion penetrates an outer layer of the skin surface responsive to the weight of the probe.

Additional features and advantages will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 2A illustrates a high level perspective cut away view of an apparatus comprising a frame, an array of fixtures and a probe, according to certain embodiments; and FIGS. 2B-2D illustrate various views of the probe of FIG. 2A.

DETAILED DESCRIPTION OF THE PREFERRED EMBODIMENTS

Figure 1A:
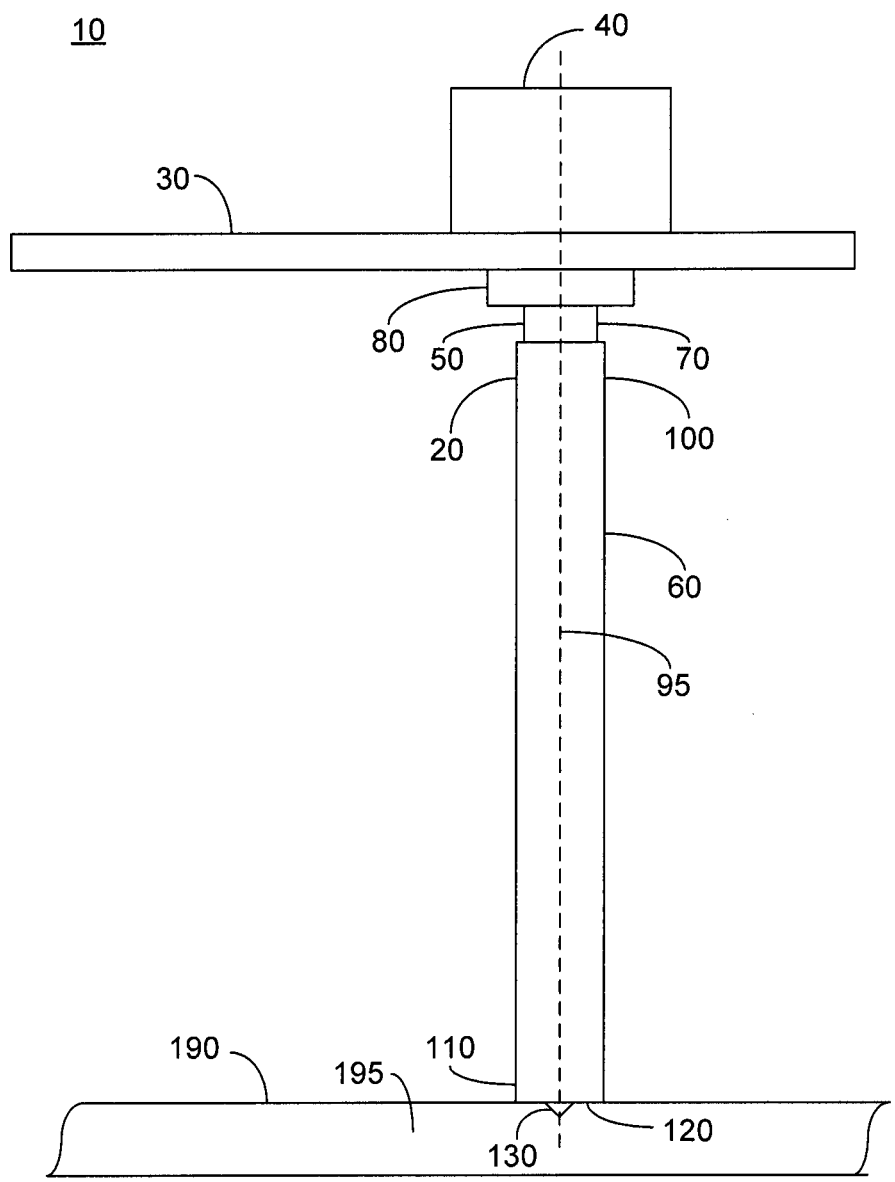
FIG. 1A illustrates a high level side view of an apparatus comprising an electrode which comprises a probe and a fixture, according to certain embodiments.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1B:
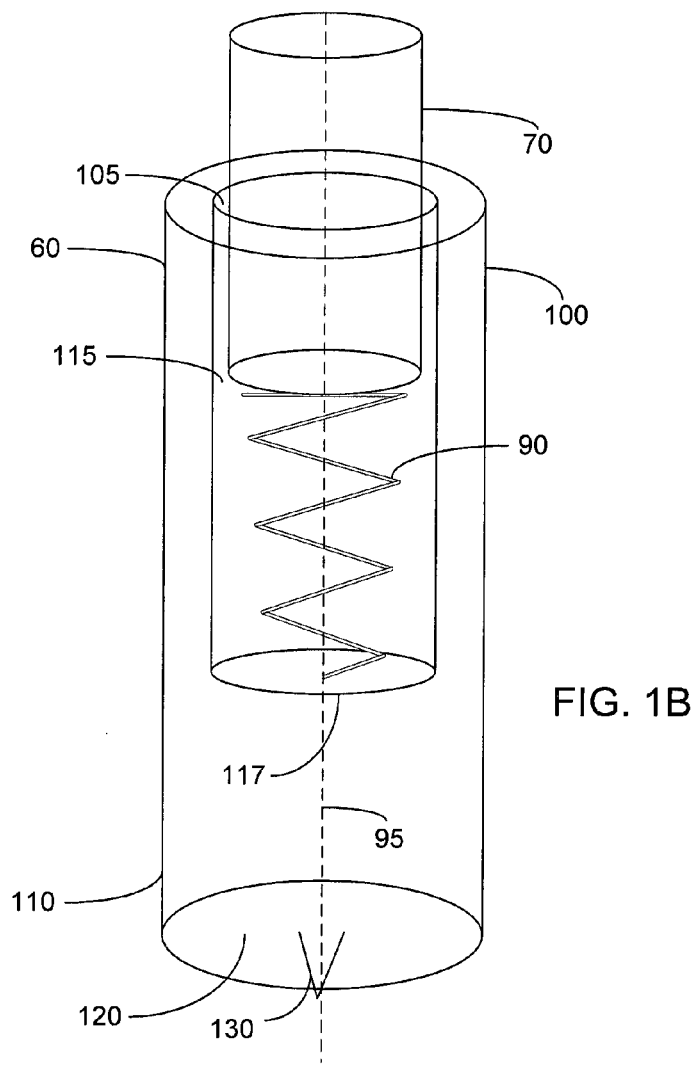
FIG. 1B illustrates a high level transparent view of the electrode of FIG. 1A according to certain embodiments.
Figure 1C:
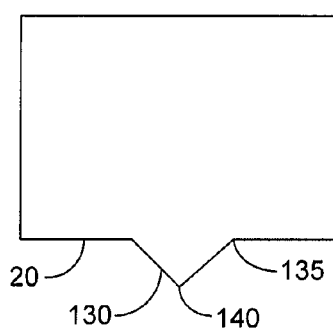
FIG. 1C illustrates a side cut view of a first embodiment of an end portion of the probe of FIG. 1A exhibiting a generally conically shaped protrusion, according to certain embodiments.
Figure 1D:
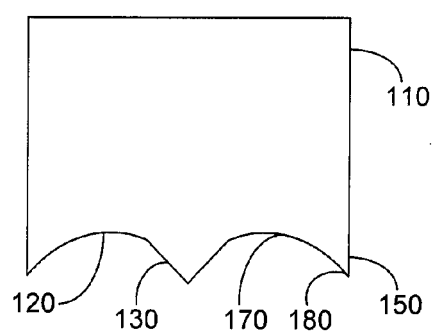
FIG. 1D illustrates a side cut view of a second embodiment of an end portion of the probe of FIG. 1A exhibiting a generally conically shaped protrusion and a perimeter protrusion, according to certain embodiments.
Figure 1E:
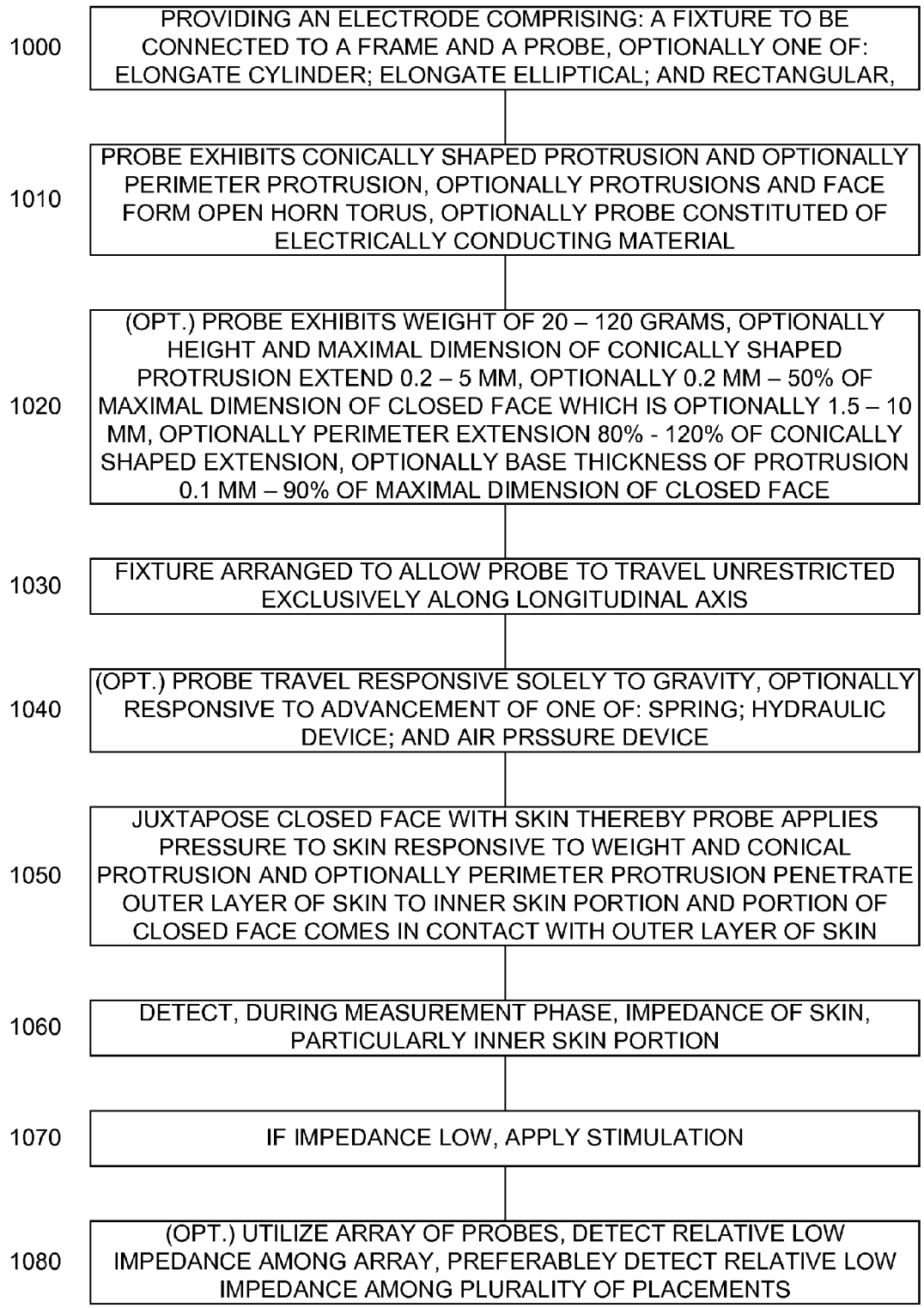
FIG. 1E illustrates a high level flow chart of a method of detecting points exhibiting low impedance and applying electrical stimulation thereto.

FIG. 1A illustrates a high level side view of an apparatus 10 comprising an electrode 20; FIG. 1B illustrates a transparent view of electrode 20; FIG. 1C illustrates a side cut view of a first embodiment of an end portion of electrode 20; FIG. 1D illustrates a side cut view of a second embodiment of the end portion of electrode 20; and FIG. 1E illustrates a high level flow chart of a method of detecting points exhibiting low impedance and applying electrical stimulation thereto, the figures being described together. Apparatus 10 further comprises: a frame 30; and an electrical measurement and electrical stimulation circuitry 40. As described in stage 1000 of FIG. 1E, electrode 20 comprises: a fixture 50; and a probe 60. Fixture 50 comprises: an elongate member 70; a base portion 80; and a coil 90. In one non-limiting illustrated embodiment, elongate member 70 is elongate cylinder shape and base portion 80 is a flange arranged to receive elongate member 70 at an internal portion thereof and secure elongate member 70 to frame 30. In another embodiment (not shown), elongate member 70 is an elongate elliptical shape and base portion 80 is elliptical shape. In another embodiment (not shown), elongate member 70 and base portion 80 are each rectangular shape. Probe 60 is in one non-limiting illustrated embodiment elongate cylinder shape and exhibits: a longitudinal axis 95; a proximal end portion 100, wherein a base 105 of probe 60 at proximal end portion 100 is at least partially open; a distal end portion 110 exhibiting a closed face 120; and a partially hollow interior 115 extending from base 105 to a point 117 proximal of distal end portion 110. The terms proximal and distal are in relation to frame 30, as will be described below. In another embodiment (not shown), probe 60 is elongate elliptical shape. In another embodiment (not shown), probe 60 is rectangular shape.

As described in stage 1010, and as seen variously in FIGS. 1B, 1C and 1D, closed face 120 exhibits a generally conically shaped protrusion 130 extending longitudinally from a base 135, consonant with closed face 120, towards an apex 140. In one embodiment, as illustrated in FIG. 1C, closed face 120 is substantially smooth with the exception of generally conically shaped protrusion 130. In another embodiment, as illustrated in FIG. 1D, closed face 120 further exhibits a perimeter protrusion 150 extending longitudinally from a perimeter area of closed face 120. Perimeter protrusion 150 proceeds in parallel with generally conically shaped protrusion 130, from a base 170 towards an edge 180. In one embodiment, generally conically shaped protrusion 130, perimeter protrusion 150 and closed face 120 generally form an open horn torus.

Coil 90 is constituted of a conductive wire thin enough to not interfere with any movement of probe 60. In one embodiment, probe 60, elongate member 70 and coil 90 are each constituted of medical grade stainless steel, in one particular embodiment the stainless steel is SS 316L. In another embodiment, probe 60, elongate member 70 and coil 90 are each constituted generally of a material exhibiting a relatively low electrical resistance, with probe 60 being constituted of material which is not dangerous to apply to the human body. In one embodiment, generally conically protrusion 130, perimeter protrusion 150 and probe 60 are formed as a unitary block.

As described in optional stage 1020, in one embodiment, probe 60 exhibits a weight of 20-120 grams, in one further embodiment about 50 grams. In one embodiment, the maximal dimension of closed face 120 is 1.5-10 mm, in one further embodiment 4 mm. The term maximal dimension is meant to define the largest chord that can be drawn across face 120, and thus: in the embodiment where probe 60 is elongate cylinder shape, the maximal dimension of closed face 120 is the diameter of closed face 120; in the embodiment where probe 60 is elongate elliptical shape, the maximal dimension of closed face 120 is the transverse diameter of closed face 120; and in the embodiment where probe 60 is rectangular shape, the maximal dimension of closed face 120 is the diagonal of closed face 120. In one embodiment, the height of generally conically shaped protrusion 130, i.e. from base 135 to apex 140, is 0.2-5 mm. In one particular embodiment, the height of generally conically shaped protrusion 130 is 0.2 mm-50% of the maximal dimension of closed face 120. In one embodiment, the maximal dimension of base 135 of generally conically protrusion 130 is 0.2-5 mm. In one particular embodiment, the maximal dimension of base 135 of generally conically protrusion 130 is 0.2 mm-50% of the maximal dimension of closed face 120. In one embodiment, the height of perimeter protrusion 150, i.e. from base 170 to apex 180, is 80%-120% of the height of generally conically shaped protrusion 130. In one embodiment, base 170 exhibits a thickness of 0.1 mm-90% of the maximal dimension of closed face 120.

In one embodiment, the length of probe 60 is 50-120 mm. In one embodiment, the length of partially hollow interior 115 is about 80 mm. In one embodiment, the maximal dimension of partially hollow interior is about 2 mm. In another embodiment, the maximal dimension of partially hollow interior is about 0.5 mm greater than the maximal dimension of elongate member 70. In one embodiment, the length of elongate member 70 is 30-60 mm.

Electrical measurement and electrical stimulation circuitry 40 is in communication with frame 30 and base portion 80 of fixture 50 is connected to frame 30. Elongate member 70 of fixture 50 is connected to base portion 80. In one preferred embodiment, base portion 80 is hollow and an end of elongate member 70 is situated within base portion 80. A second end of elongate member 70 is connected to a first end of coil 90 and a second end of coil 90 is connected to point 117 of probe 60, spring 90 situated within partially hollow interior 115.

As described in stage 1030, probe 60 and elongate member 70 are arranged such that probe 60 can extend telescopically and travel in a generally unrestricted manner exclusively along longitudinal axis 95 with respect to elongate member 70. Probe 60 is partially closed at proximal end portion 100. Elongate member 70 exhibits a protrusion at, or near, the distal end, arranged to prevent travel of probe 60 beyond a predetermined limit, since the closure of probe 60 can not travel past the protrusion.

As described in optional stage 1040, in one embodiment, probe 60 is arranged to travel along longitudinal axis 95 responsive solely to gravity. As described above, coil 90 is constituted of a very thin wire and thus does not limit the free motion of probe 60 with respect to elongate member 70. In another embodiment (not shown), an additional device is provided arranged to advance probe 60 along longitudinal axis 95, the additional device being one of: a spring; a hydraulic device; and an air pressure device. Advantageously, such an advancement mechanism ensures that each of a plurality of probes 60 exert identical force when coming into contact with a target skin surface, as will be described further below.

In operation, as described in stage 1050, frame 30 is positioned such that closed face 120 is juxtaposed with a skin surface 190, preferably with longitudinal axis 95 of probe 60 generally orthogonal to the ground. In the embodiment where probe 60 is arranged to travel along longitudinal axis 95 responsive solely to gravity, probe 60 automatically travels towards skin surface 190 and comes in contact with a particular area thereof. Preferably, substantially no substantial friction is exhibited between probe 60 and elongate member 70. Probe 60 applies force to skin surface 190 which is proportional to the weight of probe 60. In one embodiment, the force applied by probe 60 to skin surface 190 responsive to the weight of probe 60 is 0.196-1.078 N. Generally conically shaped protrusion 130 penetrates the outer layer of skin surface 190 responsive to the applied force of probe 60 and comes into contact with an inner skin portion 195, having passed through the strateum corneum of skin surface 190. The height of generally conically shaped protrusion 130 is short enough such that the penetration is shallow enough not to damage the skin and cause bleeding. Advantageously, generally conically shaped protrusion 130 provides electrical connection to inner skin portion 195, and thus electrical measurement and electrical stimulation circuitry 40 probes the impedance presented by inner skin portion 195, and not only the impedance of skin surface 190. In the embodiment where the remainder of closed face 120 is generally smooth, closed face 120 is preferably flush with skin surface 190 and applies force thereto. In the embodiment, where closed face 120 further exhibits perimeter protrusion 150, perimeter protrusion 150 penetrates the outer layer of skin surface 190 responsive to the applied force of probe 60 and provides further electrical connection to inner skin portion 195. The height of perimeter protrusion 150 is short enough such that the penetration is shallow enough not to damage the skin and cause bleeding. Preferably, the area of closed face 120 between generally conically protrusion 130 and perimeter protrusion 150 is flush with skin surface 190 and applies force thereto. Spring 90 prevents probe 60 from becoming detached from fixture 50. Additionally, as will be described below, in one embodiment spring 90 provides probe 60 with an electric path so as to provide electric voltage and current from electrical measurement and electrical stimulation circuitry 40.

As described in stage 1060, electrical measurement and electrical stimulation circuitry 40 provides a voltage during a measurement phase. Elongate member 70, spring 90 and probe 60 provide an electrical path from electrical measurement and electrical stimulation circuitry 40 to inner skin portion 195. The impedance of inner skin portion 195 is then determined. As described above, advantageously, generally conically protrusion 130 and optionally perimeter protrusion 150 protrude past the outer layer of skin surface 190 thereby electrical measurement and electrical stimulation circuitry 40 is able to measure the impedance of inner skin portion 195 which represents an improvement over measurement solely from the outer layer of skin surface 190 which typically exhibits relatively high impedance. As described in stage 1070, in the event a low impedance is detected, electrical measurement and electrical stimulation circuitry 40 provides an electrical stimulation to skin surface 190 as known to those skilled in the art. In the embodiment where closed face 120 is substantially smooth with the exception of generally conically protrusion 130, a greater portion of closed face 120 is in contact with skin surface 190, thereby providing greater electrical conductivity with skin surface 190, which is advantageous for providing the relatively large current flow required for electrical stimulation. Additionally, the size of the maximal dimension of closed face 120 is determined so as to provide greater electrical conductivity with skin surface 190.

In stage 1080, as will be described below in relation to FIGS. 2A-2D, an array of probe 60 are utilized. Preferably electrical measurement and electrical stimulation circuitry 40 is arranged to detect a relative low impedance from among the plurality of impedances detected among the array of probes 60. Further preferably electrical measurement and electrical stimulation circuitry 40 is arranged, in cooperation with a user, to detect a relative impedance from a plurality of placements of the array of probes 60, described below as array of fixtures 220 of apparatus 200. In one embodiment, relative impedances are displayed on a visual display of electrical measurement and electrical stimulation circuitry 40, and the user is directed to place array of fixtures 220 at a plurality of locations so as to detect points of relative low impedance.

FIG. 2A illustrates a high level perspective cut away view of an apparatus 200, comprising: a frame 210; an array of fixtures 220; a probe 230; and an electrical measurement and electrical stimulation circuitry 40, FIG. 2B illustrates a front view of the probe 230 of FIG. 2A and a portion of an associated fixture 220, FIG. 2C illustrates a side view of the probe 230 of FIG. 2A, and FIG. 2D illustrates an exploded view of a distal end portion 110 of the probe 230 of FIG. 2A, the figures being described together. Frame 210 exhibits: a proximal array of perforations 250; and a distal array of perforations 260. Each fixture 220 comprises: a pair of opposing slits 270; and a pair of extensions 280. Each slit is closed on both ends by frame 210. Probe 230 is in all respects similar to probe 60 of FIGS. 1A-1D, with the addition of a plurality of holes 290 as illustrated in FIG. 2D. Holes 290 allow for the connection of an external removable distal end 110 to probe 230 such that the portion of probe 230 which comes in contact with skin surface 190, i.e. distal end 110, can be replaced after each treatment thereby allowing for improved sterilization. Only one probe 230 is illustrated, however this is not meant to be limiting in any way and in another embodiment (not shown) a plurality of probes 230 are provided, each associated with a particular fixture 220. In such an embodiment, preferably each of the plurality of probes 230 exhibits substantially the same weight.

Proximal array of perforations 250 are positioned proximal of array of fixtures 220, i.e. in the direction of the operator of apparatus 200, and distal array of perforations 260 are positioned distal of array of fixtures 220, i.e. on the side of frame 210 opposing the side exhibiting proximal array of perforations 250. Probe 230 has attached thereto, on opposing sided thereof, pair of extensions 280 of an associated fixture 220. Each extension 280 is arranged to be situated within a particular one of the respective pair of opposing slits 270. Probe 230 is inserted through a respective perforation of proximal array of perforations 250 and a respective perforation of distal array of perforations 260, with proximal end 100 of probe 230 extending proximal of frame 210 and distal end 110 of probe 230 extending distal of frame 210. Electrical measurement and electrical stimulation circuitry 40 is connected to frame 210 and is in communication with probe 230. Preferably, communication between electrical measurement and electrical stimulation circuitry 40 is accomplished by means that do not interfere with the travel of probe 230. In the embodiment where a plurality of probes 230 are provided, each probe 230 is in communication with electrical measurement and electrical stimulation circuitry 40.

The arrangement of extensions 280 within slits 270 ensures that probe 230 travels solely along longitudinal axis 95 and does not rotate about longitudinal axis 95 and further does not move in any other direction. The closed ends of slits 270 ensure a maximum travel length of probe 230 along longitudinal axis 95. As described above in relation to FIGS. 1A-1D, in one embodiment probe 230 is arranged to travel along longitudinal axis 95 of probe 230 responsive solely to gravity. In another embodiment (not shown), an additional device is provided arranged to advance probe 230 along longitudinal axis 95, the additional device being one of: a spring; a hydraulic device; and an air pressure device. In operation, as described above, frame 210 is positioned such that closed face 120 of probe 230 is juxtaposed with skin surface 190 and probe 230 automatically travels towards skin surface 190 and comes in contact therewith. As described above, the force applied by probe 230 is proportional to the weight thereof. Advantageously, in the embodiment where a plurality of probes 230 are provided with each probe 230 exhibiting substantially the same weight, uniform force is provided by the plurality of probes 230 to skin surface 190 thereby allowing a more uniform and consistent measurement of the impedance across the entire skin surface 190.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. In the claims of this application and in the description of the invention, except where the context requires otherwise due to express language or necessary implication, the word "comprise" or variations such as "comprises" or "comprising" is used in any inclusive sense, i.e. to specify the presence of the stated features but not to preclude the presence or addition of further features in various embodiments of the invention.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting. No admission is made that any reference constitutes prior art. The discussion of the reference states what their author's assert, and the applicants reserve the right to challenge the accuracy and pertinency of the cited documents. It will be clearly understood that, although a number of prior art complications are referred to herein, this reference does not constitute an admission that any of these documents forms part of the common general knowledge in the art in any country.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. An electrode comprising:
a fixture arranged for connection at one end thereof to a frame; and
a probe, said probe exhibiting a closed face, a generally conically shaped protrusion extending longitudinally from said closed face towards an apex, and a perimeter protrusion extending longitudinally from the perimeter area of said closed face of said probe towards an edge, said probe in communication with said fixture, said closed face opposing said end arranged for connection to the frame,
wherein said fixture is arranged to allow said probe to travel in a generally unrestricted manner exclusively along a longitudinal axis of said probe,
wherein said generally conically shaped protrusion is arranged such that when said closed face is in contact with a skin surface outer layer said generally conically shaped protrusion is adapted to penetrate the outer layer of the skin surface responsive to the weight of said probe and to be in electrical contact with a first portion of the penetrated skin surface, and wherein said perimeter protrusion is arranged such that when said closed face is in contact with the skin surface, said perimeter protrusion is adapted to penetrate the outer layer of the skin surface responsive to the weight of said probe and to be in electrical contact with a second inner portion of the penetrated skin surface,
wherein said closed face, said generally conically shaped protrusion and said perimeter protrusion are formed as a unitary block so as to provide an electrical path, said closed face generally smooth between said generally conically shaped protrusion and said perimeter protrusion.

2. The electrode of claim 1, wherein:
the maximal dimension of the face of said probe is 1.5 - 10 millimeters, and said generally conically shaped protrusion extends longitudinally from said closed face of said probe for 0.2 millimeters - 50% of the maximal dimension of said closed face.

3. The electrode of claim 2, wherein the base of said generally conically shaped protrusion exhibits a maximal dimension of 0.2 millimeters - 50% of the maximal dimension of said closed face.

4. The electrode of claim 1, wherein said perimeter protrusion proceeds in parallel with said generally conically shaped protrusion.

5. The electrode of claim 1, wherein said generally conically shaped protrusion, said perimeter protrusion and said closed face of said probe generally form an open horn torus.

6. The electrode of claim 1, wherein the extension of said perimeter protrusion is 80% - 120% of the extension of said generally conically shaped protrusion.

7. The electrode of claim 1, wherein the base of said perimeter protrusion exhibits a thickness of 0.1 millimeters - 90% of the maximal dimension of said closed face.

8. An apparatus comprising:
a frame;
an array of fixtures, each connected to said frame at a predetermined location; and
a plurality of probes, each of said probes exhibiting a closed face, a generally conically shaped protrusion extending longitudinally from said closed face towards an apex, and a perimeter protrusion extending longitudinally from the perimeter area of said closed face of said probe towards an edge, each of said probes in communication with a particular one of said fixtures, said closed face of said probe opposing said connection of said particular fixture to said frame,
wherein each of said fixtures is arranged to allow said probe to travel in a generally unrestricted manner exclusively along a longitudinal axis of said probe,
wherein said generally conically shaped protrusion is arranged such that when said closed face is in contact with a skin surface outer layer said generally conically shaped protrusion is adapted to penetrate the outer layer of the skin surface responsive to the weight of said probe and to be in electrical contact with a first portion of the penetrated skin surface, and wherein said perimeter protrusion is arranged such that when said closed face is in contact with the skin surface, said perimeter protrusion is adapted to penetrate the outer layer of the skin surface responsive to the weight of said probe and to be in electrical contact with a second inner portion of the penetrated skin surface, wherein said closed face, said generally conically shaped protrusion and said perimeter protrusion are formed as a unitary block so as to provide an electrical path, said closed face generally smooth between said generally conically shaped protrusion and said erimeter protrusion.

9. The apparatus of claim 8, further comprising an electrical measurement and electrical stimulation circuitry, said electrical measurement and electrical stimulation circuitry in electrical communication with each of said probes.

10. An electrode comprising:
a probe, said probe exhibiting a closed face, a generally conically shaped protrusion extending longitudinally from said closed face towards an apex and a perimeter protrusion extending longitudinally from the perimeter area of said closed face of said probe towards an edge; and a means for allowing said probe to travel in a generally unrestricted manner exclusively along a longitudinal axis of said probe, wherein said generally conically shaped protrusion is arranged such that when said closed face is in contact with a skin surface outer layer said generally conically shaped protrusion is adapted to penetrate the outer layer of the skin surface responsive to the weight of said probe and to be in electrical contact with a first portion of the penetrated skin surface, and wherein said perimeter protrusion is arranged such that when said closed face is in contact with the skin surface, said perimeter protrusion is adapted to penetrate the outer layer of the skin surface responsive to the weight of said probe and to be in electrical contact with a second inner portion of the penetrated skin surface, wherein said closed face, said generally conically shaped protrusion and said perimeter protrusion are formed as a unitary block so as to provide an electrical path, said closed face generally smooth between said generally conically shaped protrusion and said perimeter protrusion.

11. The electrode of claim 10, wherein:
the maximal dimension of the face of said probe is 1.5 - 10 millimeters, and said generally conically shaped protrusion extends longitudinally from said closed face of said probe for 0.2 millimeters - 50% of the maximal dimension of said closed face.

12. The electrode of claim 11, wherein the base of said generally conically shaped protrusion exhibits a maximal dimension of 0.2 millimeters - 50% of the maximal dimension of said closed face.

13. The electrode of claim 10, wherein said perimeter protrusion proceeds in parallel with said generally conically shaped protrusion.

* * * * *